United States Patent [19]

Suzuki et al.

[11] Patent Number: 4,781,706

[45] Date of Patent: Nov. 1, 1988

[54] DEVICE FOR COLLECTING AND SELECTING EMBRYOS

[75] Inventors: Tatsuyuki Suzuki, 1, Aza-Odakurahara, Oaza-Odakura, Nishigo-mura, Nishishirakawa-gun, Fukushima-ken; Kazuhiko Masuda, Takatsuki, both of Japan

[73] Assignees: Nissho Corporation, Osaka, Japan; Tatsuyuki Suzuki, Fukushima, Japan

[21] Appl. No.: 11,946

[22] Filed: Feb. 6, 1987

[30] Foreign Application Priority Data

May 14, 1986 [JP] Japan ............................ 61-72127[U]

[51] Int. Cl.[4] ............................................... A61M 1/00

[52] U.S. Cl. .................................... 604/317; 210/460; 128/897

[58] Field of Search ................................ 604/317–320, 604/55, 127, 404, 323; 128/1 R, 760, 766, 767, 749; 210/485, 445, 446, 460; 55/484; 73/215, 216, 863.23; 422/103, 101, 102; 350/536, 535

[56] References Cited

U.S. PATENT DOCUMENTS

| | | | |
|---|---|---|---|
| 1,918,351 | 7/1933 | Schulze | 350/535 |
| 3,769,171 | 10/1973 | Grimes et al. | 350/536 |
| 4,275,732 | 6/1981 | Gereg | 604/320 |
| 4,516,973 | 5/1985 | Telang | 604/319 |
| 4,563,172 | 1/1986 | Ferguson | 128/1 R |

OTHER PUBLICATIONS

Gore Tex Membrane Products, W. L. Gore & Assoc. Elkton, Md. 21921, 1980.

Fenwal Advertising Cut (DF 381), Fenwal Laboratories Deerfield, Ill. 60015, 1983.

*Primary Examiner*—Stephen C. Pellegrino
*Assistant Examiner*—J. L. Kruter
*Attorney, Agent, or Firm*—Armstrong, Nikaido, Marmelstein & Kubovcik

[57] ABSTRACT

A device for collecting and selecting embryos comprising: an open vessel comprising a side wall and a bottom wall and made of a substantially transparent material, said side wall being provided with at least one opening; a filter means attached to said opening; and a detachable cover member capable of being tightly fastened to said vessel, said cover member being provided with an inlet for introducing a liquid containing embryos into said vessel. It is possible to carry out the collection and selection of embryos in succession without transferring the embryos to another vessel.

6 Claims, 3 Drawing Sheets

DEVICE FOR COLLECTING AND SELECTING EMBRYOS

BACKGROUND OF THE INVENTION

The present invention relates to a device for collecting and selecting embryos of a domestic animal such as cow. More particularly, it relates to a device for separating ova from a perfusate containing them, which is drawn from the uterus of an animal, by filtration, and selecting embryos by discriminating useful ova (normal embryo) from unuseful ova (nonfertilized ovum, too young embryo, abnormal embryo) through a magnifier.

Heretofore, selection of embryos in artificial insemination of domestic animal, particularly cow, has been carried out by using a device as shown in FIG. 5. A perfusate containing embryos which is drawn from the uterus of a cow is filtered by using an embryo-collecting device 10 having a metal mesh filter 11 provided at the bottom thereof. When the liquid level within the device 10 goes down to a height of 10 to 20 mm above the filter 11, the filtration is stopped by cramping a tube 13 connected to an outlet 12 of the device 10 by means of a cramp 14. The embryos attached to the filter 11 are removed by means of a pipette or the like. Thus obtained liquid containing embryos is transferred to a Petri dish or the like. The embryos were selected on the dish with being observed through a magnifier.

However, the above-mentioned conventional method has the following drawbacks. A liquid containing embryos obtained in the embryo-collecting device 10 must be transferred to another device such as Petri dish for selecting embryos. Some of the embryos attached to the filter are apt to remain as they are after the removal operation using a pipette or the like is conducted. In order to avoid the remaining of embryos, generally, the removal operation and subsequent transfer operation are repeated three times, which are troublesome and require to prepare additional embryo-selecting dishes. Further, there is a danger that embryos are lost when they are transferred from the embryo-collecting device to the embryo-selecting dish.

It is an object of the present invention to provide a simple and cheap device for collecting and selecting embryos by which both the filtration of a perfusate containing embryos and the selection of embryos can be effected without any operation for transferring a liquid containing embryos to another device.

This and other objects of the invention will become apparent from the description hereinafter.

SUMMARY OF THE INVENTION

The present invention provides a device for collecting and selecting embryos comprising: an open vessel comprising a side wall and a bottom wall and made of a substantially transparent material, said side wall being provided with at least one opening; a filter means attached to said opening; and a detachable cover member capable of being tightly fastened to said vessel, said cover member being provided with an inlet for introducing a liquid containing embryos into said vessel.

The manner of using the device of the present invention is as follows:

A perfusate containing embryos which is drawn from the uterus of a cow or other animal is introduced into the vessel through the inlet provided in the cover member. When a liquid level within the vessel rises above the lower side of the opening provided in the side wall, the filtration is started. That is, the liquid overflows through the opening. However, the embryos do not flow out due to the presence of the filter means attached to the opening. When the filtration is finished, embryos separated from a large portion of the perfusate and mucus remain within the vessel with a small portion of the perfusate. Then the cover member is detached from the vessel. Light is shone upwards to the bottom wall of the vessel. The inside of the vessel is illuminated with the transmitted light since the material of the vessel is substantially transparent. Therefore, the selection of embryos can be easily carried out in the vessel while observing with a magnifier.

DETAILED DESCRIPTION

Figure 1:
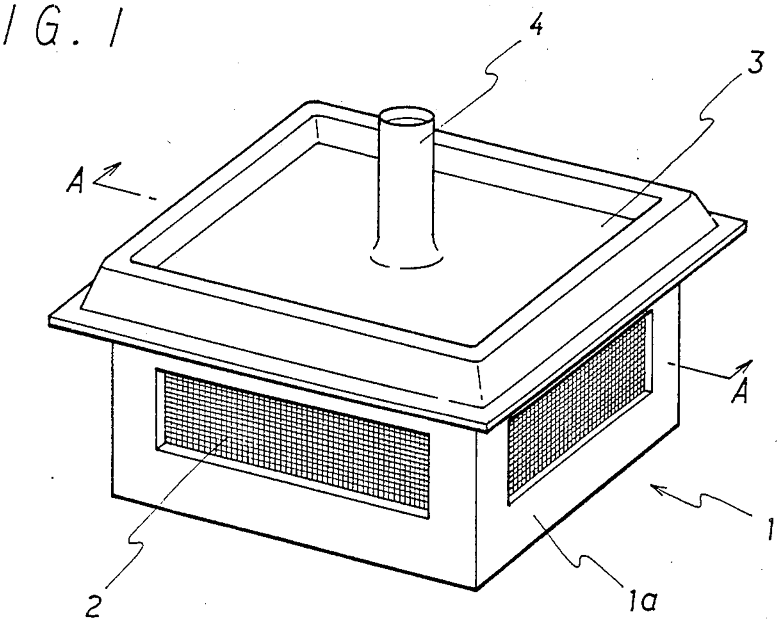
FIG. 1 is a perspective view showing an example of the device of the present invention.
Figure 3:
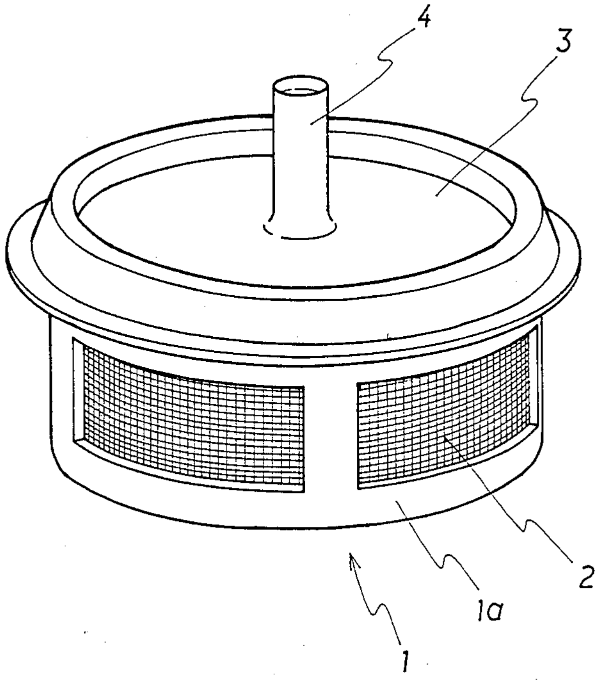
FIG. 3 is a perspective view showing another example of the device of the present invention.

Referring to the accompanying drawings, a device for collecting and selecting embryos in accordance with an embodiment of the present invention will be explained. In FIGS. 1 and 3, portions of the inside of the device which can be seen through are not described.

Figure 2:
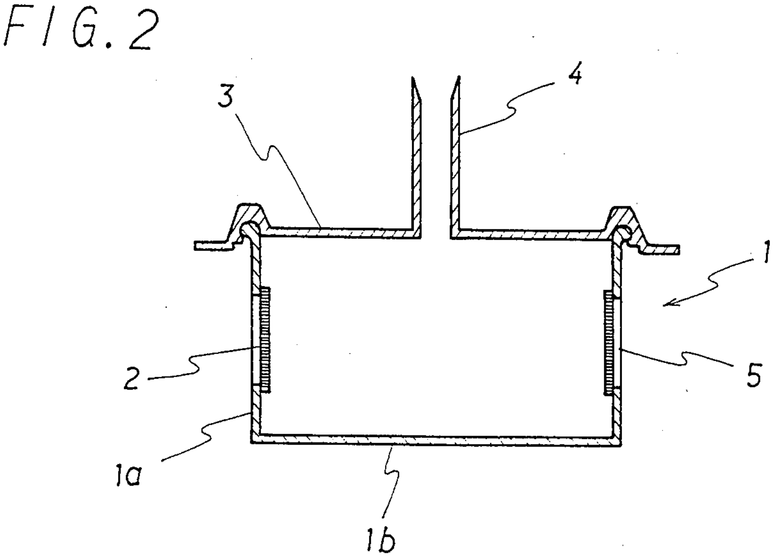
FIG. 2 is a sectional view taken along the line A—A of FIG. 1.

Referring to FIGS. 1 and 2 and FIG. 3, a device for collecting and selecting embryos in accordance with the present invention comprises an open vessel 1 comprising a side wall la and a bottom wall 1*b*, a filter 2 and a cover member 3. The cover member 3 is provided with an inlet 4 for introducing into the vessel 1 a perfusate containing embryos which is drawn from the uterus of a cow.

The vessel 1 is made of a transparent material. Examples of the transparent material include thermoplastic resins such as polystyrene, polyamide, polycarbonate, polyvinyl chloride, polymethyl methacrylate and styrene-acrylonitrile copolymer, and glass.

The side wall 1*a* is provided with one or more openings 5. The opening 5 is preferably of rectangular shape. Lines are marked at right angles on the upper surface of the bottom wall 1*b* to form squares, which makes easy the selection of embryos from unuseful ova. A size of a square is usually from 5 mm×5 mm to 10 mm×10 mm. When embryos are observed through a magnifier, it is preferable that one square is seen in the visual field of the magnifier. When a magnifier of 16 magnifications is used, a square size of 7 mm×7 mm is preferred.

Figure 4:
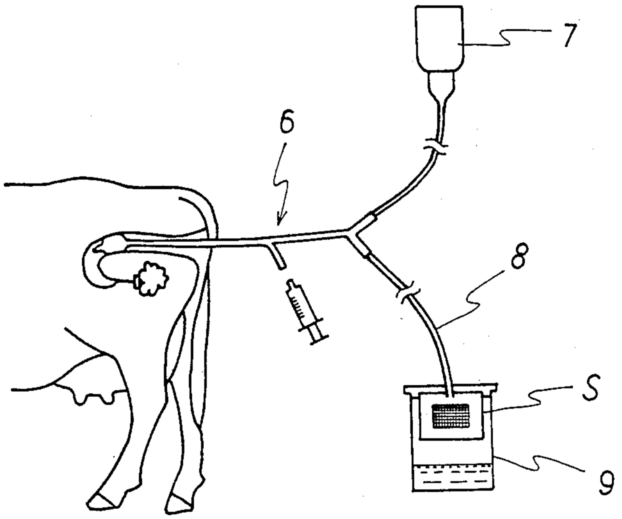
FIG. 4 is an explanatory view showing a manner of using the device of the prevent invention.
Figure 5:
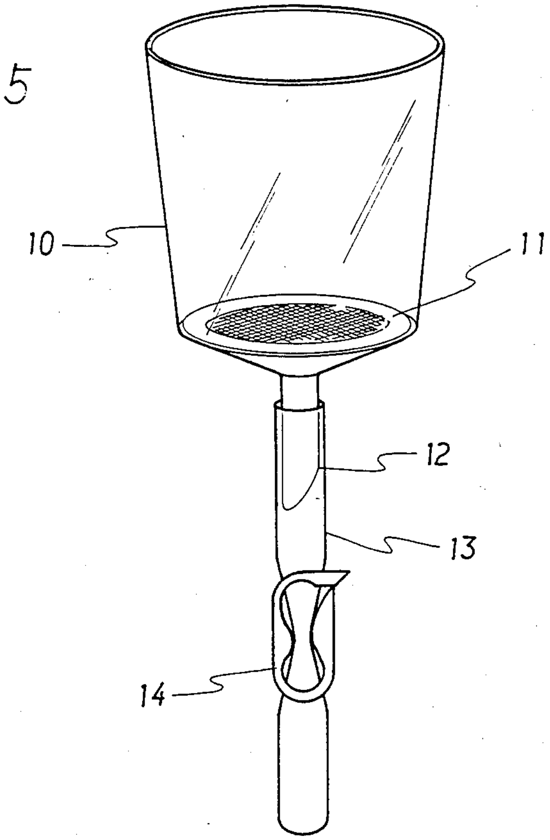
FIG. 5 is a perspective view showing a conventional embryo-collecting device.

Any vessel 1 having a cross-section such as rectangle, circle, ellipse or polygon can be used. From the standpoint that the filter 2 is easily attached to the opening 5, a vessel 1 having a cross-section of square as shown in FIG. 1 or hexagon is preferred. When the device of the present invention is used, it is mounted on a filtrate container 9 as shown in FIG. 4. Usually the filtrate container has a circular cross-section. Therefore, from the standpoint that the device of the present invention is easily mounted on such filtrate container, a vessel 1 having a cross-section of circle as shown in FIG. 3 is preferred.

The opening 5 is preferably of rectangular shape. The rectangular opening 5 is preferably provided such that the lower side of the rectangular opening is positioned at 5 to 15 mm distance from the bottom wall 1*b* of the vessel 1. When the distance is smaller than 5 mm, the depth of the liquid within the vessel 1 is too shallow, which invites the drying of embryos. When the distance is larger than 15 mm, the depth of the liquid within the vessel 1 is too deep, which makes the selection of embryos difficult.

A filter 2 covering the opening 5 is preferably fixed to the inner surface of the side wall la by means of adhesive. A mesh filter and a filter in the form of layer, such as filter cloth can be used as a filter 2. However, a mesh filter is preferred due to easy mounting and low cost. A net of synthetic fibers such as polyamide filaments and polyester filaments and a net of metal wires are preferably used as a mesh filter. In the case of collecting embryos of cow, a mesh filter having an opening size of not more than 120 μm is preferably used, because embryos of cow have a size of about 150 μm to about 200 μm. A mesh filter having an opening size of 70 to 90 μm is more preferred so that even deformed embryos do not pass through the filter and a high filtering rate is achieved.

A cover member 3 is preferably made of a transparent or translucent material. Examples of such material include thermoplastic resins such as polyethylene, polypropylene, polyamide, polycarbonate, polyester, polyvinyl chloride and styrene-acrylonitrile copolymer, and the like.

The cover member 3 is tightly fastened to the vessel 1 so that there is formed no clearance between the cover member 3 and the upper end of the side wall 1*a*.

Preferably an inlet 4 is formed such that the inlet 4 and a catheter for drawing embryos from the uterus of a cow can be connected with a tube to introduce directly a perfusate containing embryos from the catheter to the inside of the vessel 1. For instance, the inlet 4 is of tubular shape. A tubular inlet 4 is usually provided so that it errects from the central portion of the cover member 3.

A tubular inlet 4 may be integrally formed with the cover member 3. Alternatively, a tubular inlet 4 formed separately may be fixed to the cover member 3. The tubular inlet 4 is also made of a thermoplastic resin, etc.

A manner of using the device of the present invention will be explained by referring to FIG. 4.

A device S in accordance with the present invention is connected with a connecting tube 8 to a balloon catheter 6 for collecting a perfusate containing embryos from the uterus of a cow.

A perfusate contained in a perfusate container 7 is introduced into the uterus of a cow through a balloon catheter 6 inserted into the uterus and the uterus is washed with the perfusate so that embryos are suspended in the perfusate. The perfusate containing embryos is introduced into the device S through the balloon catheter 6 and the connecting tube 8. The perfusate containing embryos is filtered and the embryos are collected in the device S. Most portion of the perfusate overflows and flows into a filtrate container 9. The cover member 3 is removed from the vessel 1 and the vessel 1 is placed under a magnifier for selection of embryos.

As is clear from the descriptions described above, the present invention has the following advantages.

(1) It is possible to carry out the collection of embryos and the selection thereof in succession in one vessel with ease.

(2) The device of the present invention is structually simple and has two functions in combination, which provides an economical advantage.

(3) An operation of transferring embryos from one device to another device which encounters with the conventional method is not required. Therefore, there is no danger that embryos are lost in operations of the collection and selection of embryos.

It is to be understood that the present invention is not limited to the above Example, and various change and modifications may be made in the invention without departing from the spirit and scope thereof.

In addition to the elements used in the Example, other elements can be used in the Example as set forth in the specification to obtain substantially the same results.

What is claimed:

1. A device for collecting embryos from an embryo-containing perfusate, which is drawn from the uterus of an animal, and selecting the collected embryos, comprising: an open vessel comprising a side wall and a bottom wall and made of a substantially transparent material, said side wall being provided with at least one opening, said opening being at a distance from the bottom wall; a filter means attached to said opening, said filter means permitting the passage of liquid while retaining embryos; and a detachable cover member capable of being tightly fastened to said vessel, said cover member being provided with an inlet for introducing said embryo-containing perfusate into said vessel.

2. The device of claim 1, wherein the filter means comprises a mesh filter having an opening size of not more than 120 μm.

3. The device of claim 1, wherein the opening of the side wall is of rectangular shape.

4. The device of claim 3, wherein said rectangular opening is provided such that the lower side of the rectangular opening is positioned at 5 to 15 mm distance from the bottom wall of the vessel.

5. A device for collecting embryos from an embryo-containing perfusate, which is drawn from the uterus of an animal, and selecting the collected embryos, comprising: an open vessel comprising a side wall and a bottom wall and made of a substantially transparent material, said side wall being provided with at least one opening, said opening being at a distance from the bottom wall, and said bottom wall being marked with lines to form squares; a filter means attached to said opening, said filter means permitting the passage of liquid while retaining embryos; and a detachable cover member capable of being tightly fastened to said vessel, said cover member being provided with an inlet for introducing said embryo-containing perfusate into said vessel.

6. The device of claim 1, wherein lines are marked on the inner surface of the bottom wall to form squares each having a size of 5 mm×5 mm to 10 mm×10 mm.

* * * * *